(12) United States Patent
Hayden

(10) Patent No.: US 9,400,236 B2
(45) Date of Patent: Jul. 26, 2016

(54) MAGNETOPHORETIC ANALYTE SELECTION AND CONCENTRATION

(75) Inventor: Oliver Hayden, Herzogenaurach (DE)

(73) Assignee: Siemens Aktiengesellschaft, München (DE)

( * ) Notice: Subject to any disclaimer, the term of this patent is extended or adjusted under 35 U.S.C. 154(b) by 147 days.

(21) Appl. No.: 14/118,175

(22) PCT Filed: May 11, 2012

(86) PCT No.: PCT/EP2012/058814
§ 371 (c)(1),
(2), (4) Date: Nov. 15, 2013

(87) PCT Pub. No.: WO2012/156324
PCT Pub. Date: Nov. 22, 2012

(65) Prior Publication Data
US 2014/0087414 A1    Mar. 27, 2014

(30) Foreign Application Priority Data

May 18, 2011    (DE) .......................... 10 2011 076 051

(51) Int. Cl.
*G01N 1/40*    (2006.01)
*B01L 3/00*    (2006.01)
*G01N 27/74*    (2006.01)
*B03C 1/28*    (2006.01)

(52) U.S. Cl.
CPC ............ *G01N 1/40* (2013.01); *B01L 3/502761* (2013.01); *B03C 1/286* (2013.01); *B03C 1/288* (2013.01); *G01N 27/745* (2013.01); *B01L 2200/0652* (2013.01); *B01L 2300/0654* (2013.01); *B01L 2300/0816* (2013.01); *B01L 2300/0864* (2013.01); *B01L 2400/043* (2013.01); *B01L 2400/086* (2013.01); *B03C 2201/18* (2013.01); *B03C 2201/26* (2013.01)

(58) Field of Classification Search
CPC .................. B01L 2400/043; B01L 3/502761; B01L 2200/0636; B01L 2300/0864; B01L 2200/0647; B01L 2200/0652; B01L 2200/0668
See application file for complete search history.

(56) References Cited

U.S. PATENT DOCUMENTS

| 7,223,371 B2 | 5/2007 | Hayenga et al. |
| 2002/0036141 A1 | 3/2002 | Gascoyne et al. |
| 2003/0000835 A1 | 1/2003 | Witt et al. |

(Continued)

FOREIGN PATENT DOCUMENTS

| DE | 10320869 A1 | 12/2004 |
| DE | 102004062534 A1 | 7/2006 |

(Continued)

OTHER PUBLICATIONS

Jung Jinhee et al. Applied Physics Letters, AIP vol. 93, No. 1, Dec. 1, 2008, pp. 223902(-1)-22390(-3)).*

(Continued)

*Primary Examiner* — Sally Merkling
(74) *Attorney, Agent, or Firm* — Lempia Summerfield Katz LLC

(57) ABSTRACT

Devices and methods for magnetophoretic analyte selection and concentration are described. Magnetically marked analytes (e.g., cells) may be separated out of a sample dynamically in flux, such that the magnetically marked analytes are present in a highly concentrated manner in a reduced sample volume. The analyte selection may be followed by an analysis.

14 Claims, 4 Drawing Sheets

(56) References Cited

U.S. PATENT DOCUMENTS

| | | | |
|---|---|---|---|
| 2003/0175980 | A1 | 9/2003 | Hayenga et al. |
| 2007/0020767 | A1 | 1/2007 | Schnelle |
| 2007/0207548 | A1* | 9/2007 | Blankenstein ............ 436/63 |
| 2008/0124779 | A1* | 5/2008 | Oh .............. B01L 3/502761 435/173.9 |
| 2011/0059556 | A1* | 3/2011 | Strey ............ B01L 3/502761 436/518 |
| 2012/0187938 | A1 | 7/2012 | Bar et al. |

FOREIGN PATENT DOCUMENTS

| | | |
|---|---|---|
| DE | 60311968 T2 | 11/2007 |
| DE | 102009005925 A1 | 7/2010 |
| DE | 102009047801 A1 | 3/2011 |
| WO | 2011038982 A1 | 4/2011 |

OTHER PUBLICATIONS

Jung et al.(Applied Physics Letters 93, 223902 (2008)).*

Chengxun Liu et al., "Cell Manipulation with Magnetic Particles Toward Microfluidic Cytometry", Journal of Applied Physics, 2009, 12 pages, vol. 105, No. 10, American Institute of Physics.

German Office Action dated Jun. 19, 2012 in corresponding German Patent Application No. DE 10 2011 076 051.2 with English translation.

International Search Report and Written Opinion in PCT/EP2012/058814 dated Jul. 17, 2012 with English translation.

Jinhee Jung et al., "Lateral-Driven Continuous Magnetophoretic Separation of Blood Cells", Applied Physics Letters, Dec. 1, 2008, 3 pages, vol. 93, No. 22, American Institute of Physics.

Nikola Pekas et al., "Magnetic Particle Diverter in an Integrated Microfluidic Format", Journal of Magnetism and Magnetic Materials, 2005, pp. 584-588, vol. 293.

* cited by examiner

MAGNETOPHORETIC ANALYTE SELECTION AND CONCENTRATION

RELATED APPLICATIONS

This application is the National Stage of International Application No. PCT/EP2012/058814, filed May 11, 2012, which claims the benefit of German Patent Application No. DE 102011076051.2, filed May 18, 2011. The entire contents of both documents are hereby incorporated herein by reference.

TECHNICAL FIELD

The present teachings relate to magnetophoretic analyte selection and enrichment.

BACKGROUND

Cells may represent analytes of interest. Optical measuring methods (e.g., scattered light or fluorescence measurements) and magnetic detection methods (e.g., for detecting a cell type marked by magnetic labels) have been used for cell measurement and cell detection.

For magnet-based measurements, magnetically marked cells may be sorted from a complex cell suspension (e.g., a blood sample) by magnetophoresis. The magnetic marking is achieved by introducing cell-specific markers into the complex cell sample. Magnetophoresis has been used for sorting magnetically marked cells and magnetic particles.

Cell measurements in diagnostics and science involve measuring cell types (e.g., disseminated tumor cells) that are only present in a blood sample in very small concentrations. Thus, the loss of cells during sample preparation is undesirable. To quantify cell concentrations or to reliably detect specific cells, a prior enrichment of the cells to be determined from a suspension with a complex background is performed.

Enrichment of cells has been performed using centrifuging techniques, immunochromatography, and magnetic enrichment (MACS). In such methods, the enrichment takes place statically (e.g., the cells are enriched on a vessel wall or in a portion of a centrifuge tube). The enrichment factor observed using such methods may lie in a range of $10^1$ to $10^4$ and is not sufficiently high. For example, in the case of centrifuging techniques, mechanical loading of the cells may be unavoidable.

Conventional methods of magnetophoresis for dynamic cell enrichment tend to provide a low enrichment factor that does not exceed an enrichment of 100-fold. An example of magnetophoresis in a laminar flow is described by Jung et al. in *Applied Physics Letters*, 2008, 93, 223902.

SUMMARY AND DESCRIPTION

The scope of the present invention is defined solely by the appended claims, and is not affected to any degree by the statements within this summary.

The present embodiments may obviate one or more of the drawbacks or limitations in the related art. For example, in some embodiments, the concentration of analytes to be detected in a sample suspension may be increased by magnetophoretic analyte selection and enrichment.

A device for magnetophoretic analyte selection and enrichment in accordance with the present teachings includes a flow channel, a first magnetic unit configured for the enrichment, and a second magnetic unit configured for the alignment of magnetically marked analytes. In some embodiments, the enrichment and alignment of the analytes is provided in a first portion of the flow channel, and the first portion of the flow channel includes the magnetic units. The separation takes place in the second portion of the flow channel. In the second portion of the flow channel, the flow channel divides into at least two part-channels. A first of these part-channels runs in a third portion of the flow channel. The first part-channel has a smaller cross-sectional area than the flow channel in the first portion of the flow channel. Magnetically marked analytes may be introduced in the first part-channel with a smaller cross-sectional area. The sample volume per length of portion located in the first part-channel is thus much smaller than in the flow channel with the large cross-sectional area. This reduction of the sample volume facilitates higher concentration.

In some embodiments, the magnetic units provide three-dimensional enrichment and guidance of magnetically marked analytes, thereby facilitating the above-described reduction in sample volume by the geometry of the flow channel. The narrowing of the flow channel in the direction of flow allows enrichment factors greater than 100 to be achieved.

In some embodiments, the first part-channel has a cross-sectional area in the third portion of the channel that is less than one-half of the cross-sectional area of the flow channel in the first portion of the flow channel. In some embodiments, the first part-channel has a cross-sectional area in the third portion of the channel that is less than one-tenth of the cross-sectional area of the flow channel in the first portion of the flow channel. In some embodiments, the first part-channel is a microfluidic channel.

In some embodiments, analyte selection and enrichment is performed on cells in complex media (e.g., blood samples). The analyte (e.g., the cells) may have varying diameters between 1 and 20 μm. In some embodiments, white blood cells measure between 7 and 12 μm in diameter. In some embodiments, for cell selection and enrichment, the cell types have diameters of about 3 μm (e.g., platelets). In some embodiments, the cell types have diameters between 8 and 12 μm. By way of example, CD4+ cells have a diameter of about 7 μm. However, even within a cell type, diameters vary. Tumor cells may have a diameter of 10 to 20 μm. Magnetically marked polymeric spheres (e.g., beads) may have diameters of between 100 nm and 20 μm. In some embodiments, small analytes (e.g., viruses) may also be enriched.

An analyte sample may be passed through a much wider (e.g., 10 to 1000 times in diameter) microfluidic channel. In some embodiments, channel diameters of 10 μm to 10,000 μm may be realized. The lower value (e.g., the minimum diameter) may be limited by the analyte diameter. The upper value may be limited by establishing a laminar flow in the channel.

In some embodiments, a second part-channel has a cross-sectional area (and/or a plurality of additional part-channels has a total cross-sectional area) that is sufficiently large to transport a sample volume arriving through the flow channel in the first portion of the flow channel to the part-channels in the third portion of the channel. Marked analytes may be selected from the present sample volume, and the larger second part-channel may transport away the present sample volume after selection of the marked analytes. This diversion of the sample volume prevents velocity gradients in the sample flow and, for example, disturbing turbulences.

In some embodiments, the cross-sectional area of the second part-channel and/or the total cross-sectional area of the multiple second part-channels is sufficiently large that the flow behavior of the sample volume is not significantly influenced. In other words, the second part-channel or the multiple second part-channels may be designed such that the enrichment and alignment of magnetically marked analytes in the sample volume is not disturbed. In some embodiments, the diameter of the second part-channel is between 100 μm and 10,000 μm.

In some embodiments, the first part-channel in the third portion of the flow channel runs in the same direction as the flow channel in the first portion thereof. Thus, veering away of the direction of flow for the sample to be selected may be avoided. The part of the sample volume that is not to be selected may be deflected from the original direction of the first portion of the channel. This configuration positively impacts flow behavior.

In some embodiments, the first magnetic unit is arranged in the first portion of the flow channel, such that a magnetic gradient field is produced that enriches magnetically marked analytes within the flow channel at the bottom thereof.

In some embodiments, the bottom of the flow channel in the first part-channel in the third portion is at the same height as the bottom of the flow channel in the first portion. The smooth progression of the bottom of the channel through the part-portions avoids undesirable influencing of the flow.

In some embodiments, the second magnetic unit is arranged in the first portion of the channel, such that magnetically marked analytes within the flow channel may be aligned along an axis that continues in the third portion of the flow channel to run within the first part-channel. Thus, in the first portion of the flow channel, the magnetically marked analytes may be aligned with an axis that conducts the magnetically marked analytes straight into the first part-channel.

In some embodiments, a channel feed to the first part-channel may be provided in the third portion of the channel. A channel feed provided after the portion of the channel for analyte separation may be used to feed a second marking to the analytes. For example, the channel feed may be used for feeding additional markers to the analytes (e.g., attached by antibodies). The channel feed may be used if the first part-channel feeds the selected analytes (e.g., cells) directly to a measuring device. In some embodiments, the third portion of the channel contains the channel feed.

In some embodiments, a device for analyte selection and enrichment further includes an analyte detection device or an analyte counting device. In some embodiments, a device includes a magnetoresistive sensor arranged at the end of the second portion of the flow channel or in the third portion of the flow channel.

In some embodiments, the enrichment and guidance of the magnetically marked analytes may be influenced by the type of magnetic markers and/or by the flow velocity established in the device. The flow velocity may be set by microfluidic dimensioning. The enrichment and guidance may be optimized using the magnetophoretic guiding lines. In some embodiments, the magnetophoretic guiding lines may be arranged with respect to magnetic permeability and the angle of flow direction, and a strict alignment of the magnetically marked analytes may be achieved. The magnetic gradient field that may be produced by the first magnetic device may also be used to optimize the enrichment of a specific type of analyte (e.g., a specific cell type).

In some embodiments, a device may have a cascaded arrangement of multiple magnetophoretic enrichment and selection sections of a type described above. A series of multiple (in some embodiments differently designed) enrichment and selection sections may be provided one behind the other.

In some embodiments, a flow of a sample with magnetically marked analytes is produced. The magnetically marked analytes of the sample are dynamically enriched and aligned in a magnetic gradient field. The magnetically marked analytes are thus concentrated in a partial volume of the sample. The partial volume is dynamically separated from the remaining volume of the sample. The dynamic enrichment (e.g., in concentration) of the analytes in a sample (e.g., a cell suspension) allows the analytes (e.g., cells) to be so highly concentrated in a stress-free manner (e.g., without mechanical loading) such that the analyte may be quantified and measured.

In some embodiments, the enrichment and alignment of the magnetically marked analytes is performed three-dimensionally in a flow channel. The enrichment thus takes place on the inner wall of the flow channel by a first magnetic unit, and the alignment takes place along an axis by a second magnetic unit. The axis runs in the direction of flow along the inner wall of the channel. This three-dimensional enrichment and alignment facilitates passage of the selected analytes into a part-channel that holds a much smaller volume than the enrichment flow channel.

In some embodiments, further markers are fed to the selected analytes (e.g., cells). The additional markers may have antibodies that may attach to characteristic isotopes on the cell surface. The cells magnetically marked for selection may be provided with further markers that may be used for further cell measurement. In some embodiments, the cells additionally marked may be passed on directly for further cell measurement. The enrichment, alignment, and subsequent selection may take place using a device in accordance with the present teachings by injecting a cell sample into the device.

As a result of the above-described dynamic enrichment, cells may be passed on for further analysis in a stress-free manner (e.g., by mechanical loading). For example, after the selection, a fluorescence marking may take place, and microscopy or flow cytometry may be performed with low marker consumption.

Since the selection and enrichment may be coupled directly to a subsequent process act or investigation act, analysis time may be advantageously reduced, and sample transfer may be avoided. Sample loss (e.g., loss of marked analytes) in concentration determinations may be reduced. In addition, consumables (e.g., pipette tips) may likewise be reduced.

BRIEF DESCRIPTION OF THE DRAWINGS

The terms "left," "right," "top," and "bottom" as used herein are not intended in an absolute sense but rather, for the sake of convenience, are used in reference to the alignment of the drawing figures (e.g., in landscape orientation as shown).

DETAILED DESCRIPTION

Figure 1:
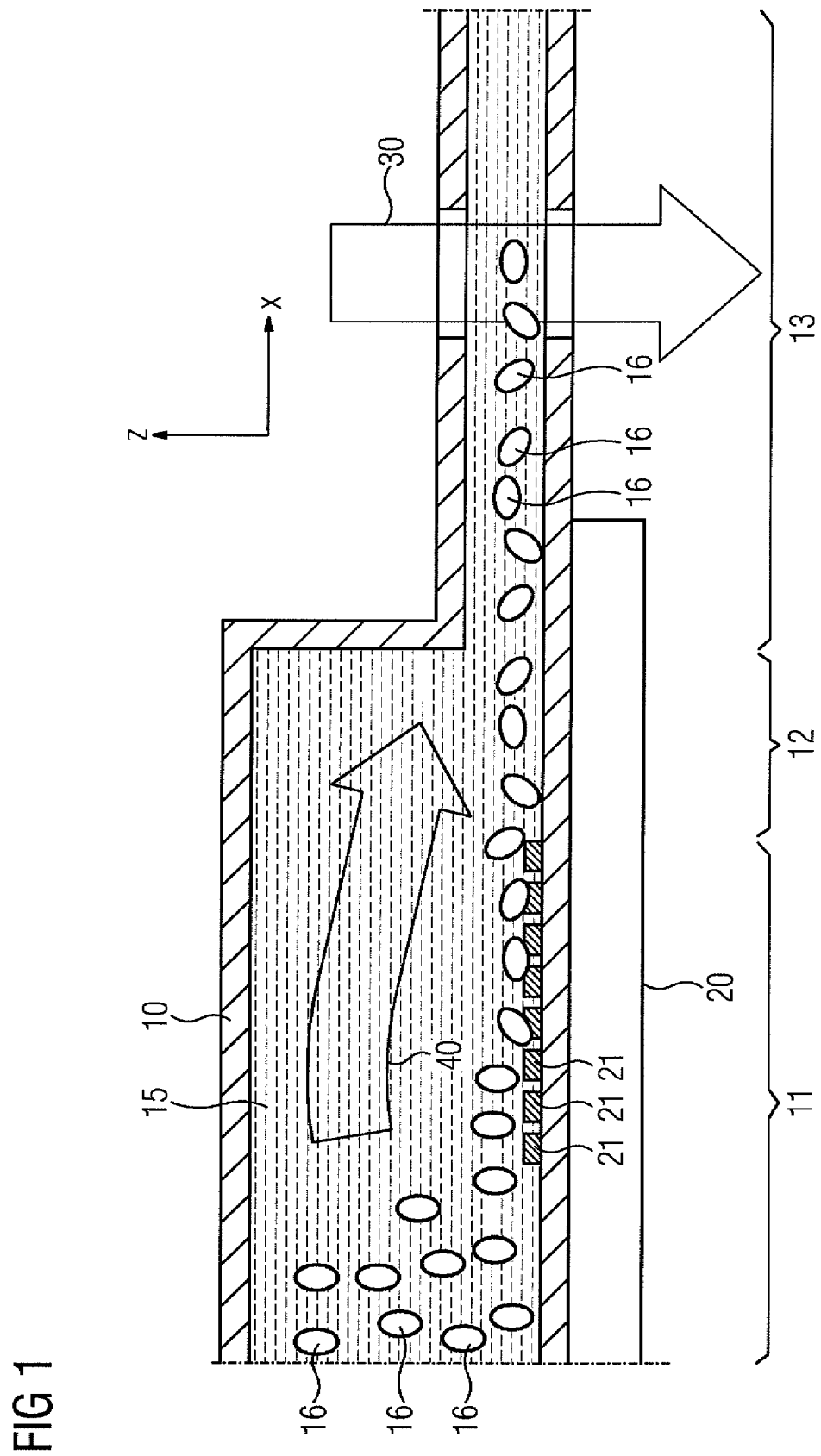
FIG. 1 shows a cross-section of an exemplary flow channel.

FIG. 1 shows a cross-section through a flow channel 10. A suspension 15 (e.g., a blood sample) flows through the flow channel 10 from left to right. The direction of flow is indicated by an arrow 40. On the left side of the channel 10, there is at least one inlet for the sample 15. On the right side of the channel 10, there is at least one outlet. The suspension 15 contains at least one type of cells 16 carrying magnetic markers. The magnetically marked cells 16 are first deflected in the left portion of the channel 10 by a permanent magnet 20 attached below the bottom of the channel. The magnetically marked cells 16 are deflected towards the bottom of the channel and are thereby enriched on the bottom of the channel. The portion of the channel 10 with the permanent magnet 20 is referred to as the enrichment section 11. The enrichment section 11 serves for the alignment of the magnetically marked cells 16. For this purpose, an additional magnet 21 may be provided above the bottom of the channel (e.g., on the inner side of the channel). In other embodiments, the additional magnet 21 may be recessed into the bottom of the channel. Ferromagnetic strips 21 are suitable for the alignment of the magnetically marked cells 16. In FIG. 1, the ferromagnetic strips 21 are shown in cross section as guiding lines running into the plane of the drawing.

After the alignment and enrichment section 11, the magnetically marked cells 16 are separated from the rest of the suspension 15. The selection region 12 contains multiple outflow directions 40, as best shown by the plan view in FIG. 2. As best shown in FIG. 1, the channel 10 narrows at the end of the separating section 12 to a microfluidic channel 13. Substantially only the magnetically marked cells 16 flow through the microfluidic channel 13 in a small sample volume 15. A detection device 30 is shown in the region of the microfluidic channel 13. In some embodiments, the detection device 30 is a microscopy or flow cytometry device. By coupling analytic capabilities in this manner, stress-free selected and enriched cells 16 may be provided.

Figure 2:
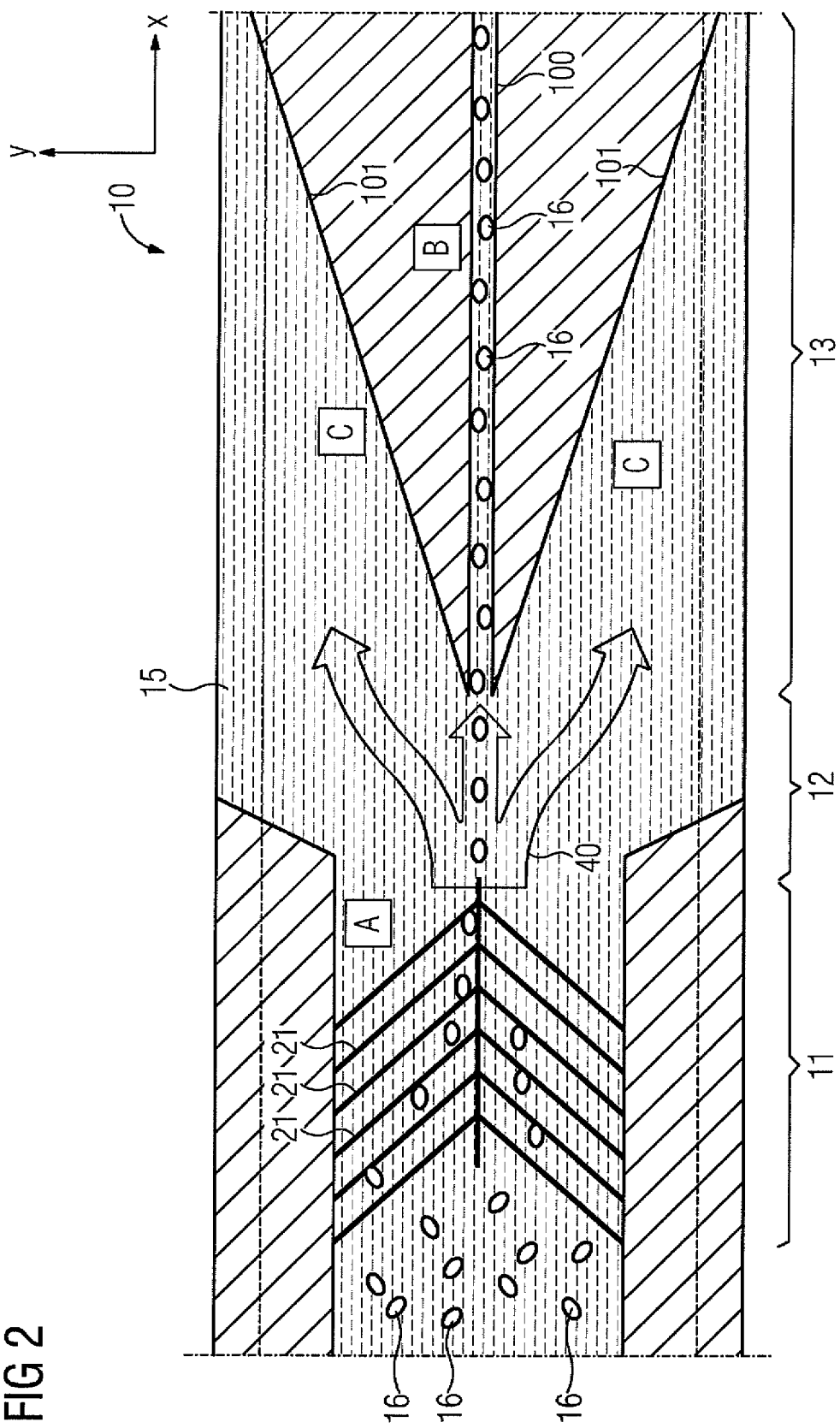
FIG. 2 shows a plan view of an exemplary flow channel.

FIG. 2 shows a plan view of the channel 10 with three portions: the alignment and enrichment section 11, the separating section 12, and the microfluidic section 13. On the left side of the channel 10, in the region of the enrichment section 11, the ferromagnetic guiding lines 21 are arranged in a herringbone structure leading the magnetically marked cells 16 toward the center of the channel. Thus, concentration takes place in the plane. At the same time, the magnetically marked cells 16 are brought near the bottom of the channel by the permanent magnet 20 (not shown) attached underneath the channel 10. The permanent magnet 20 covers the third dimension in the enrichment. In the region of the separating section 12, the enriched and aligned cells 16 flow into the microfluidic channel 101. The microfluidic channel 101 contains a much smaller sample volume 15 than the remaining channel 10. To the side of the microfluidic channel 100, the cell sample 15 may also flow to the left and the right, as indicated by the three directions of flow designated by arrow 40. In some embodiments, the part-sections 101 run to the left and right of the microfluidic channel 100 in a y-shaped manner away from the central direction of flow. In some embodiments, the entire channel volume 15 or the channel geometry is configured to prevent turbulences in the flow 40 that could disturb the magnetic enrichment and alignment (e.g., in the region of the separation 12). Accordingly, the outflow regions 101 include a sufficiently large sample volume 15 to compensate for the narrowing of the microfluidic channel 100. As shown in the front-end view of FIG. 3, the enrichment section is identified as A, the microfluidic section as B, and the lateral outflow sections as C.

Figure 3:
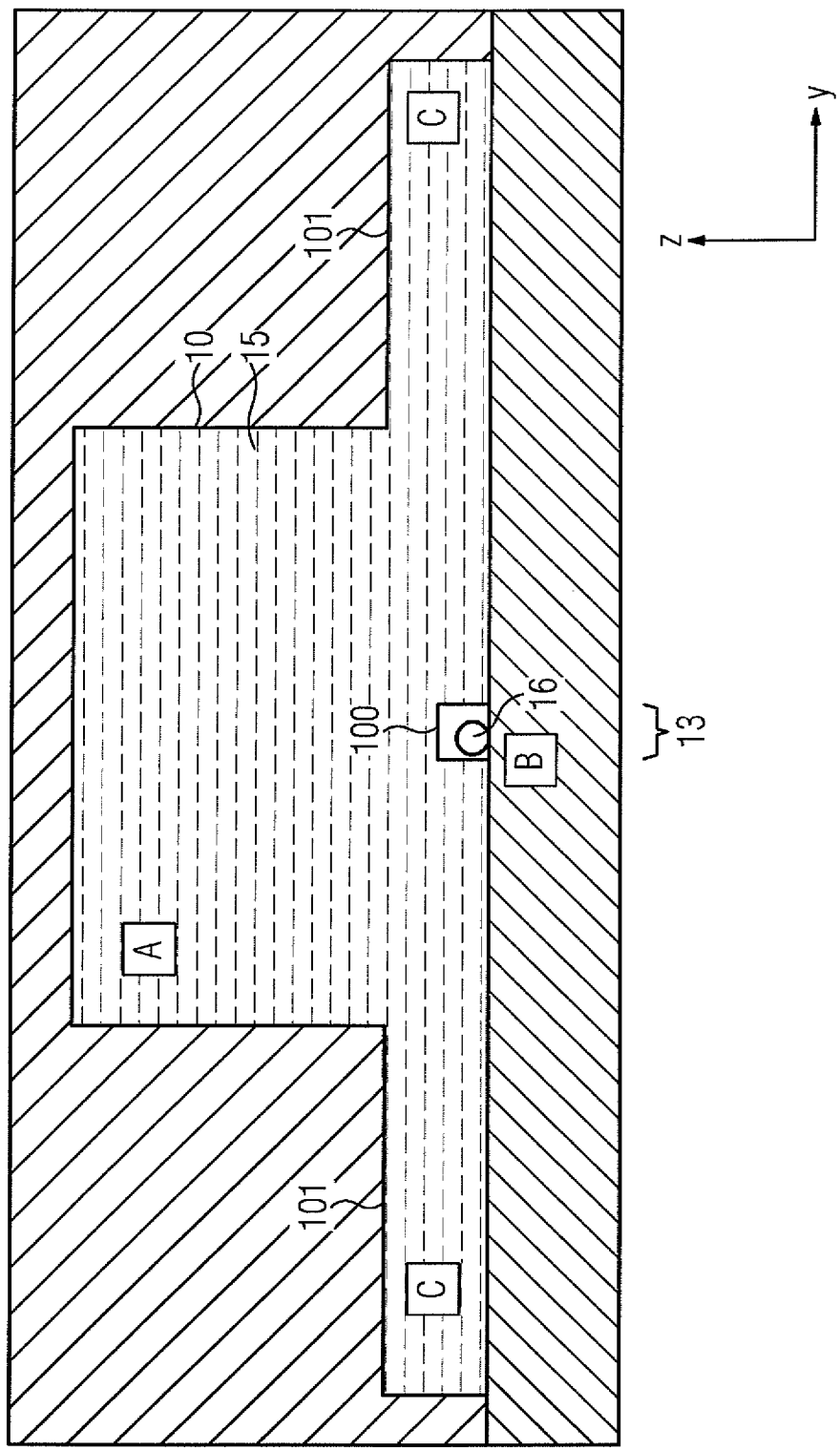
FIG. 3 shows a front-end view of an exemplary flow channel.

The front view of FIG. 3 is not an illustration to scale of the different cross sections of the enrichment flow channel A, the microfluidics section B, and the outflow sections C to the left and right of the microfluidics section B. The schematic representation shown in FIG. 3 is intended to illustrate that the microfluidic channel 100 is sufficiently narrow that the magnetically marked cells 16 may take up a large part of the channel volume 15 (e.g., are highly concentrated). An analytical device 30 coupled to the microfluidic channel 100 facilitates highly reliable individual cell detection.

Figure 4:
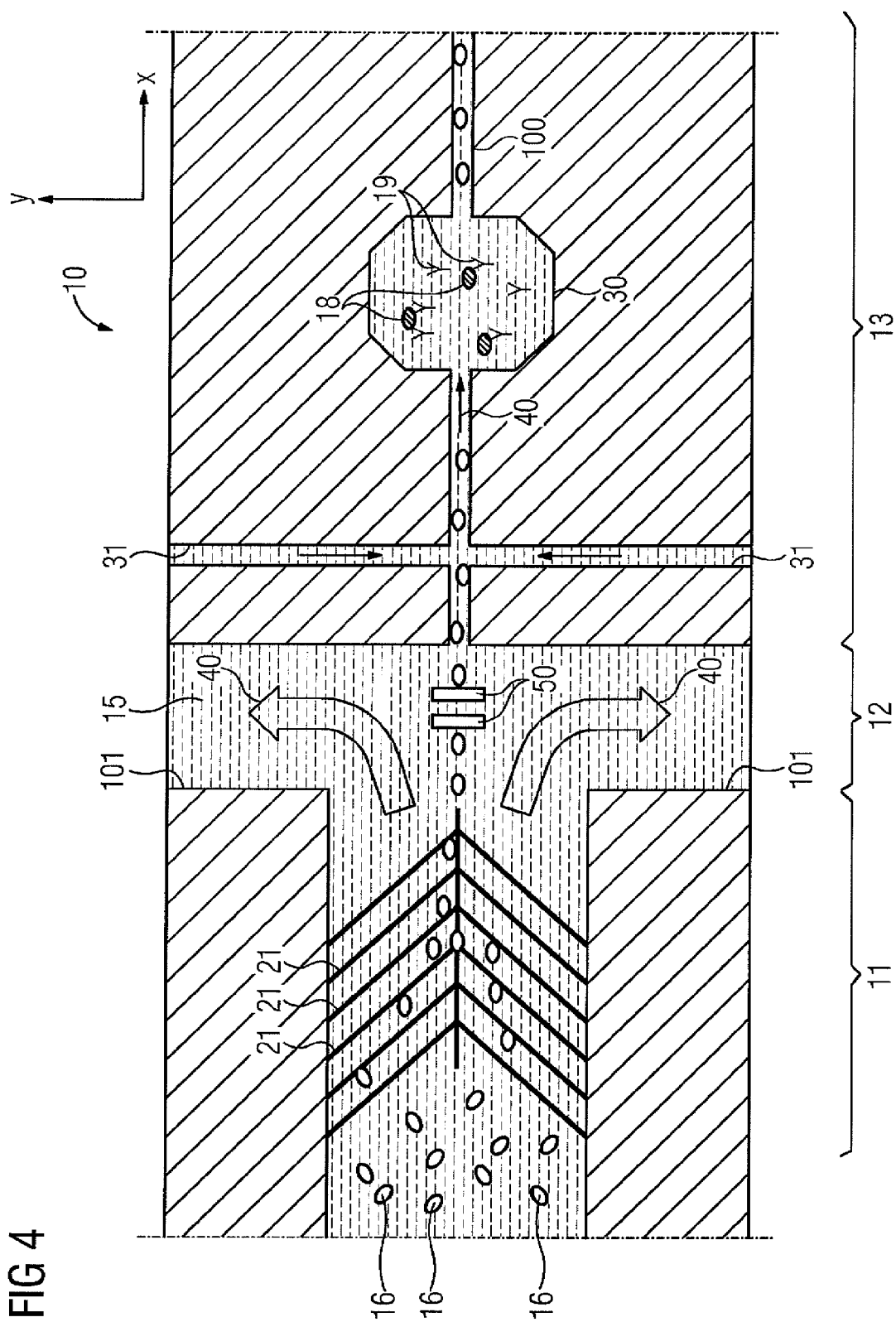
FIG. 4 shows a plan view of an exemplary flow channel.

FIG. 4 shows a plan view of the flow channel 10. Analogous to the embodiment shown in FIG. 2, the flow channel 10 with the magnetic enrichment and alignment section in the first part-portion 11 shares a common axis with the part-channel 100 into which the magnetically marked cells 16 are conducted. In the second portion of the channel 12, where the separation of the magnetically marked cells 16 from the suspension 15 takes place, the part-channels 101 run away perpendicularly from the flow channel 10. The part-channels 101 have a substantially greater width than the part-channel 100. In some embodiments, the part-channel 100 is a microfluidic channel. Apart from the perpendicular leading away of the part-channels 101 that take up the main part of the original sample liquid 15, the embodiment shown in FIG. 1 further differs from the y-shaped flow channel 10 shown in FIG. 2 in the channel feeds 31 that meet the part-channel 100 on both sides. In some embodiments, the channel feeds 31 are configured for the feeding of additional markers 19. Once the magnetically marked cells 16 are introduced into the part-channel 100 by the enrichment at the bottom of the channel and by the magnetophoretic alignment along the magnetic guiding lines 21, the magnetically marked cells 16 are provided with additional markers 19. The additional markers 19 prepare the cells 16 for further cell measurement 30. The twice-marked cells 18 are conducted by the microfluidic channel 100 into a cell-measuring device 30. In some embodiments, the additional markers 19 may be fluorescence markers and, in some embodiments, the cell measuring device 30 may include fluorescence detection.

While the present invention has been described above by reference to various embodiments, it should be understood that many changes and modifications may be made to the described embodiments. It is therefore intended that the foregoing description be regarded as illustrative rather than limiting, and that it be understood that all equivalents and/or combinations of embodiments are intended to be included in this description.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding claim—whether independent or dependent—and that such new combinations are to be understood as forming a part of the present specification.

The invention claimed is:

1. A device for magnetophoretic analyte selection and enrichment, the device comprising:
    a flow channel having a first section, a second section, and a third section, wherein the second section is positioned between and adjacent to the first section and the third section such that the second section links the first section and the third section, and wherein the flow channel splits into at least a first part-channel and a second part-channel in the second section of the flow channel;
    a first magnetic unit arranged in the first section of the flow channel, wherein the first magnetic unit produces a magnetic gradient field that enriches magnetically marked analytes within the flow channel at a bottom of the flow channel; and
    a second magnetic unit arranged in the first section of the flow channel, wherein the second magnetic unit aligns the magnetically marked analytes within the flow channel along an axis that continues in the first part-channel of the third section, such that the first part-channel in the third section and the flow channel in the first section extend along the same axis, and wherein the first part-channel in the third section of the flow channel has a cross-sectional area that is smaller than a cross-sectional area of the flow channel in the first portion.

2. The device as claimed in claim 1, wherein the cross-sectional area in the third section of the flow channel is less than one-half of the cross-sectional area of the flow channel in the first section of the flow channel.

3. The device as claimed in claim 1, wherein the second part-channel has a cross-sectional area, or multiple second part-channels have a total cross-sectional area configured to transport a sample volume arriving through the flow channel in the first section to the first part-channel and the second part-channel in the third section.

4. The device as claimed in claim 3, wherein the cross-sectional area of the second part-channel or the total cross-sectional area of the multiple second part-channels is configured such that a flow behavior of the sample volume is uninfluenced, and the enrichment and the aligning of the magnetically marked analytes in the sample volume is not disturbed.

5. The device as claimed in claim 1, wherein a height of the bottom of the flow channel of the first part-channel in the third section and a height of the bottom of the flow channel in the first section are equal.

6. The device as claimed in claim 1, further comprising a channel feed to the first part-channel in the third section of the flow channel.

7. The device as claimed in claim 1, further comprising an analyte measuring device in the third section of the flow channel.

8. The device as claimed in claim 1, wherein the cross-sectional area in the third section of the channel is less than one tenth of the cross-sectional area of the flow channel in the first section of the channel.

9. The device as claimed in claim 1, wherein the flow channel splits into a plurality of part channels comprising the first part channel, the second part channel, and at least one additional part channel, and wherein the plurality of part channels has a total cross-sectional area configured to transport a sample volume arriving through the flow channel in the first section to the plurality of part-channels in the third section.

10. The device as claimed in claim 9, wherein the total cross-sectional area is configured such that a flow behavior of the sample volume is uninfluenced, and the enrichment and the aligning of the magnetically marked analytes in the sample volume is not disturbed.

11. The device as claimed in claim 7, wherein the analyte measuring device is configured for cell measurement.

12. The device as claimed in claim 6, wherein the channel feed is configured to provide additional markers to the magnetically marked analytes.

13. The device as claimed in claim 12, wherein the additional markers are fluorescence markers.

14. The device as claimed in claim 13, further comprising an analyte measuring device in the third section of the flow channel, wherein the analyte measuring device comprises fluorescence detection.

* * * * *